(12) United States Patent
Fernandez (10) Patent No.: US 8,515,989 B2
(45) Date of Patent: Aug. 20, 2013

(54) DYNAMIC DATA MANAGEMENT SYSTEM AND METHOD FOR COLLECTING DATA FROM DISPERSE SOURCES IN REAL-TIME

(76) Inventor: Ronald E. Fernandez, Ann Arbor, MI (US)

( * ) Notice: Subject to any disclaimer, the term of this patent is extended or adjusted under 35 U.S.C. 154(b) by 5 days.

(21) Appl. No.: 13/025,250

(22) Filed: Feb. 11, 2011

(65) Prior Publication Data

US 2011/0202556 A1 Aug. 18, 2011

Related U.S. Application Data

(60) Provisional application No. 61/303,760, filed on Feb. 12, 2010.

(51) Int. Cl.
*G06F 7/00* (2006.01)
(52) U.S. Cl.
USPC ............ 707/769; 707/802; 707/809; 707/940
(58) Field of Classification Search
None
See application file for complete search history.

(56) References Cited

U.S. PATENT DOCUMENTS

| | | | | |
|---|---|---|---|---|
| 2002/0103811 | A1* | 8/2002 | Fankhauser et al. | 707/104.1 |
| 2006/0106787 | A1* | 5/2006 | Fernandez | 707/4 |
| 2008/0046292 | A1* | 2/2008 | Myers et al. | 705/3 |
| 2009/0006483 | A1 | 1/2009 | Fernandez | |
| 2010/0088117 | A1* | 4/2010 | Belden et al. | 705/3 |

OTHER PUBLICATIONS

"Public Governance Models for a Sustainable Health Information Exchange Industry", *Report to the State Alliance for E-Health*—provided by University of Massachusetts Medical School Center for Health Policy and Research (CHPR), National Opinion Research Center (NORC), and National Governors Association Center for Best Practices, Feb. 2009, 64 pages.

* cited by examiner

*Primary Examiner* — Anh Tai Tran (57) ABSTRACT

A dynamic system and a method for locating and obtaining patient information in real-time is provided. The system generally comprises an order in the form of a query; a document management and storage system (DMSS); at least one tool that is capable of sending the query to a server in order to retrieve available information; a communication channel; and a data collection and conversion system (DCCS). The DMSS includes both an application processor and a tool processor designed to manage and control the storage of electronic documents through the use of an application program that includes functionality for selecting the tool and authenticating the order.

25 Claims, 3 Drawing Sheets

DYNAMIC DATA MANAGEMENT SYSTEM AND METHOD FOR COLLECTING DATA FROM DISPERSE SOURCES IN REAL-TIME

RELATED APPLICATIONS

This application claims the benefit of U.S. Provisional Application Ser. No. 61/303,760 filed on Feb. 12, 2010, entitled "DYNAMIC DATA MANAGEMENT SYSTEM AND METHOD FOR COLLECTING DATA FROM DISPERSE SOURCES IN REAL-TIME," the entire contents of which are incorporated herein by reference.

FIELD

This disclosure relates generally to the field of data collection, and more specifically to a novel, dynamic system and method for collecting data from disperse data sources using data collection tools that function through an automated interface.

BACKGROUND

Specific information relevant to the health of a patient may be stored in files, records, and other data sources located in many different medical facilities such as physician offices, hospitals, skilled nursing facilities, medical laboratories, free standing radiology clinics and other health care providers. Patient information is often required by organizations that are authorized to receive such information, such as medical service provider plans, governmental agencies, including Medicare and Medicaid, and other authorized organizations. The specific information may be found in many locations, on various media, in numerous formats and amid a considerable amount of non-relevant data. For example, data collection may take the form of extracting data from electronic or paper files and records or collecting data visually by inspection during an on-site audit of a medical facility. Selecting, collecting, abstracting, and organizing the relevant data into a format that is readily analyzed and managed by the resources of a medical service provider plan or other authorized organization is a complex and time consuming task. Thus, authorized organizations have a need for new and efficient systems and methods for selecting, collecting, abstracting, organizing, and managing specific medical information from the files of their participating medical and healthcare service providers.

SUMMARY

In satisfying the above need, as well as overcoming the enumerated drawbacks and other limitations of the related art, the present disclosure provides a dynamic system for locating and obtaining patient information in real-time. The system generally comprises an order in the form of a query; a document management and storage system (DMSS); at least one tool that is capable of sending the query to a server in order to retrieve available information; a communication channel; and a data collection and conversion system (DCCS). The query requests information regarding a specific patient or group of patients. The information resides as source information, which includes both a data collection routine and a tool collection routine. The DMSS includes both an application processor and a tool processor designed to manage and control the storage of electronic documents through the use of an application program. The application program includes functionality that can select a tool and authenticate the order. The communication channel allows communication between the application processor and the tool processor; while the DCCS links the tool with both the DMSS and the source information. The DMSS may when desirable reside at a remote site from the source information.

The order, which is in the form of executable code, machine readable code, script, or pseudo-code, may be used to identify a list of the possible locations in which the source information resides. The query provides individual questions or a group of questions to be answered, a description of the type of information being sought, and/or the identification of a desirable response type. The response type may be a yes/no answer, a predetermined numeric value range, or an alpha text.

The DMSS can reside on a server that is different than the server on which the source information is located. This second server is in communication with the first server through the communication channel. The software run by the application processor as part of the DMSS may be, for example, ProData™, EHMDS, or Almaga™. The tool may be a collection of script when desirable. The tool may also be a collection of tools that represent a compilation of all the different variations in which the query may be represented. It is the authentication functionality that enables predetermined data collection assignments to be correlated with the request or order.

The DCCS may reside on another separate server. This third server may be in communication with the other first and second servers via the communication channel. The DCCS links the tool processor and source information through the use of a generic interface. The DCCS is compatible with industry standard formats, including but not limited to, continuity care documents (CCD), continuity of care records (CCR), and HL7 messaging. When desirable, the DCCS may be D3™.

The tool collection routine of the source information includes at least one data tool linked to a data set that contains parameters, information, or data, which can assist the tool collection routine in using the data tool. The tool processor includes a data store in which data records and data tools are stored and a tool parsing engine that is used to execute instructions that form the code or script of the data tools. The communication channel may be a dedicated facility, a wide area network (WAN), a virtual private network (VPN), a local area network, or the internet.

According to another aspect of the present disclosure, a health care directive registry is provided that includes more than one organization as a member with each member maintaining a server that incorporates source information; and the dynamic system described herein. The dynamic system is used to locate and obtain patient information in real-time from the source information maintained by the members of the registry. The members of the registry may include a hospital, a medical provider, an insurance agency, a medical organization, a clinic, or the Department of Health.

According to another aspect of the present disclosure, a health information exchange (HIE) is provided that comprises a disperse network of more than one participant as a member with each member maintaining at least one server that includes source information; and the dynamic system described herein. The dynamic system is used to locate and obtain patient information in real-time from the source information maintained by the members of the HIE. The participants in the HIE may include health care directive registries, healthcare payers, laboratories, hospitals, designated web portals, diagnostic imaging facilities, medication intermediaries, public health agencies, ambulatory EHRs, or PHRs/health record banks.

According to yet another aspect of the present disclosure, a method for collecting data from source information is provided. The method generally comprises: an interface application logging onto an application program that resides on an application processor or tool processor in response to a query; the application program authenticating the interface application; the interface application requesting appropriate tools for a specific data collection assignment; the application program retrieving the assignment for the interface application; the application program building a tool set with script for each tool that will enable the interface application to collect the data from the source information; the tool set being sent to the tool processor; the tool processor executing the script for each tool necessary to collect the data from the source information; the interface application collecting the desired data; and the tool processor uploading information to a data receiver and collecting the data in a database. In this method, the data collection is performed in real-time.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is in no way intended to limit the present disclosure or its application or uses. It should be understood that throughout the description and drawings, corresponding reference numerals indicate like or corresponding parts and features.

The current disclosure generally, provides a dynamic system that provides a secure, real-time method of locating and obtaining patient information stored as part of a health care directive registry or over a more disperse network, such as a health information exchange (HIE). This dynamic system provides the ability to have the application residing at a remote site that can query and retrieve information in response to the query or multiple queries from multiple databases. The type of information that is sought may include, but not be limited to medical and legal documents submitted by individuals or on behalf of individuals and stored in electronic format in one or more databases located at or managed by hospitals, medical providers, insurance agencies, medical organizations, clinics, and the Department of Health, among others. Examples of such documents include Health Care Power of Attorney, Advance Directive, Declaration of Anatomical Gift, and other medical documents.

Figure 1:
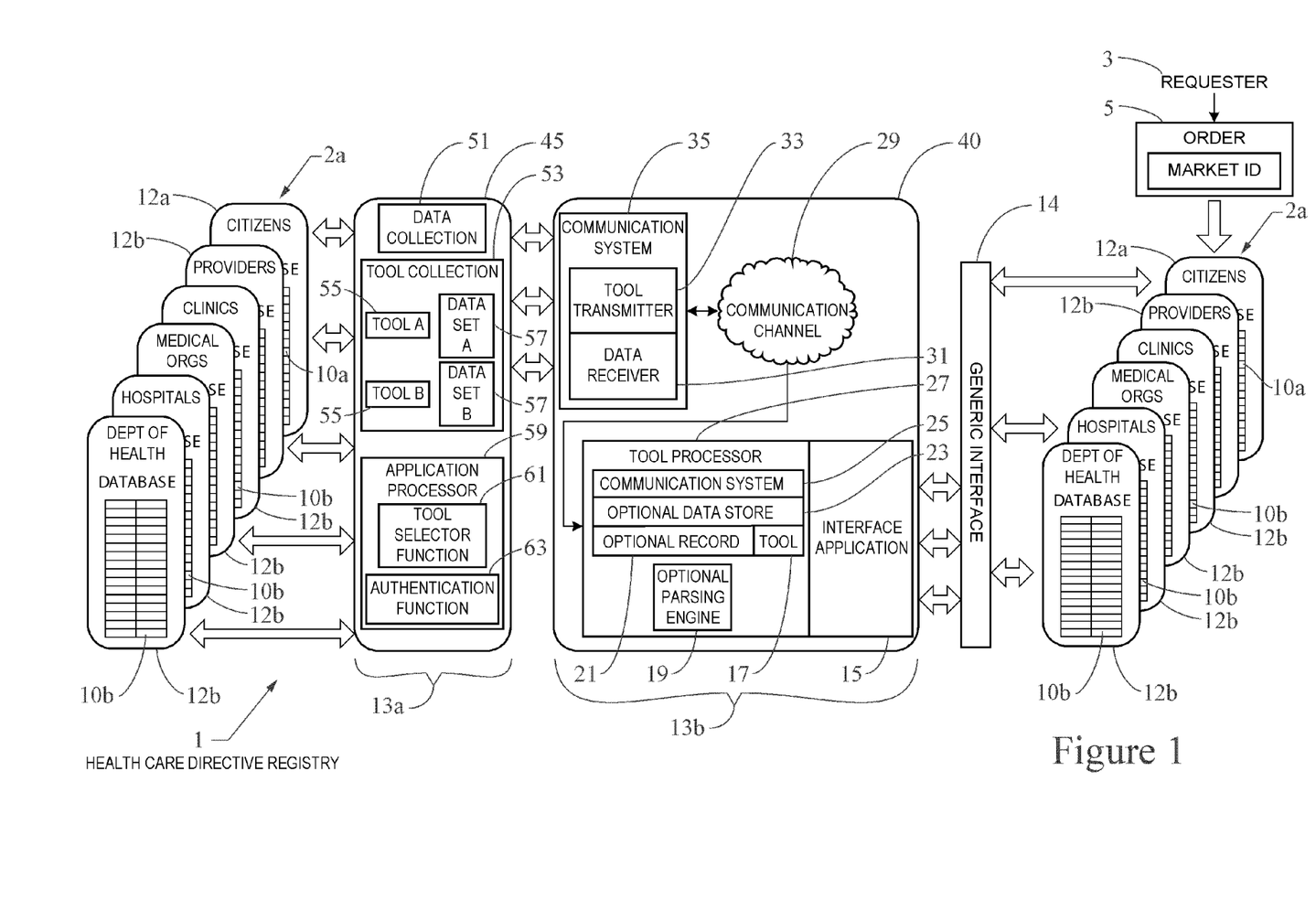
FIG. 1 is a schematic representation of the architecture and functional entities exhibited by a dynamic system prepared according to the teachings of the present disclosure.

As shown in FIG. 1, the system 1 comprises a user or requester 3 that submits a request or an order 5 for information regarding a specific individual or group of individuals in a health care directive registry 2a. The requestor 3 may be a citizen associated with the advanced directive registry or an organization associated with the registry, such as an authorized hospital (e.g., admitting hospital or emergency room, etc.), medical providers, medical organizations, insurance agencies, clinics, or the Department of Health, among others. The information being sought may reside as source information 10a located on a server 12a managed or maintained by the requestor 3 and/or as source information 10b located on a server 12b managed and maintained by another organization within the registry. Thus at times, the requestor 3 may be both the source of the request 5 and the organization within the registry that has the information being sought and collected in response to the request 5.

The request 5 represents executable code, machine readable code, script, or pseudo-code associated with a provider and/or a specific query regarding an individual or group of individuals. The request 5 may utilize language and provide queries used to identify a list of all possible database locations in which the information being sought may reside. Examples of such language and queries include, but are not limited to those known as a "where" clause or "if" clause as used in a variety of different software, such as Microsoft Access®. Part of the code associated with the request 5 may include a method that identifies the requestor 3, provides individual questions or group of questions to be answered, describes the type of information being sought, and/or identifies a desirable response type, such as a yes/no answer, a predetermine numeric value range, or an alpha text.

The server 12(a-b) includes source information 10(a-b) that is comprised of various tables and fields. These tables and fields include information regarding various individuals and groups of individuals. Examples of information that may be included in the source information 10(a-b) include, but are not limited to personal health records and the medical or legal documents as described above. This information may reside in various formats or media types, such as in a Microsoft Excel® worksheet or as a scanned document in which the text of the document has been rendered electronically recognizable through any means known to one skilled in the art, such as through the use of optical character recognition (OCR) software. These tables and fields may include the information being sought by the request or order 5 submitted by the requestor 3.

The server 12(a-b) is linked to a document management and storage system (DMSS) 13a. The DMSS 13a includes one or more other servers 45 that are in communication with server 12(a-b), as well as in communication with an application processor 59 and/or a tool processor 27. The DMSS 13a includes software designed to manage and control the storage of electronic documents through the application processor 59. An example of such software is commercially available as ProData™ (Unival Inc., Ann Arbor, Mich.). If desirable other software, such as that conventionally used as part of an electronic health data management system (EHDMS) or Microsoft Almaga™ could be utilized in place of ProData™. The application processor 59 has a tool selector functionality 61 for selecting tools appropriate for a given data collection assignment and an authentication functionality 63 to identify particular requestors 3 who input a query 5 through the tool processor 27. A tool represents a collection of script or information necessary to send out a query to locate and request data from the source information. A compilation of the all the different variations in which a query or question may be represented defines a collection of tools or a tool set.

The authentication functionality 63 enables particular, predetermined data collection assignments to be correlated with the correct request or order 5. The authentication function 63 acts a security layer by maintaining a signature key for each of the various applications in the system 1. This function identifies and authorizes particular queries attempting to interface with the tool processor 27, thereby, enabling and assigning specific data collection requests 5 to the system 1.

The server 12(*a-b*) is also linked to an advanced data collection and conversion system (DCCS) 13*b*, such as that commercially available as D3™ (Unival Inc., Ann Arbor, Mich.). The DCCS 13*b* includes one or more other servers 40 that are in communication with server 12(*a-b*) and the DMMS 13*a*. The DCCS 13*b* can communicate with handheld devices or other types of mobile devices to quickly and accurately extract data from paper or electronic medical records, data warehouses, and other data streams or stores. The DCCS 13*b* also provides links between the tool processor 27 and the DMMS 13*a* through a communication system 35 and channel 29, as well as between the tool processor 27 and source information 10 on the server 12(*a-b*) through a generic interface 14.

The DCCS 13*b* is preferably a multiple-application system such that it can, when desirable, simultaneously produce comprehensive, customized web-based reports for every data collection request 5. The DCCS 13*b* can collect the data at the point-of-care, from remote locations, or from electronic documents directly uploaded into the DCCS 13*b*. The DCCS 13*b* preferably works with industry standard formats, such as continuity of care documents (CCD), continuity of care records (CCR), or HL7 Messaging, among others to allow for interoperability with any standard electronic health record system.

A further description of the DMSS 13*a* and DCCS 13*b* included as part of system 1 in the current disclosure is provided in U.S. Pat. No. 7,519,622 issued to R. Fernandez on Apr. 14, 2009 and in U.S. patent application Ser. No. 12/231,176 filed on Aug. 29, 2008 entitled "System and Method for Collecting Data from Data Sources and Using Data Collection Tools," the entire contents of which are hereby incorporated by reference.

The application processor 59 may reside on the same server 12(*a-b*) as source information 10(*a-b*) or be physically separated from the information 10(*a-b*) and reside on a separate server 45. The source information 10(*a-b*) includes both a data collection 51 and a tool collection 53 routine. The tool collection 53 routine includes at least one data tool 55, but could contain a multiple different data tools 55A, 55B, etc. for use in collecting data. Each data tool 55 is linked or associated with a data set 57. Each data set 57 contains parameters, information, and data that assists in the execution or use of the associated or linked data tool 55.

The communication system 35 includes both a tool transmitter 33 for transmitting the data tools 55 and data sets 57 to the tool processor 27 and a data receiver 31 for receiving data records that are based on information contained in the source files or database 10(*a-b*) identified as a result of the request or order 5. The data records are stored in the data collection 51 routine residing on the server 45 as part of the DMSS 13*a*. The communication system 35 allows the application processor 59 to communicate through a communication channel 29 with the tool processor 27 and the tool processor 27 to communicate with remote servers 12*b*.

The tool processor 27 is an application program residing in the DCCS 13*b* that sends the query to where the data is stored.

The tool processor 27 may optionally include a data store 23 in which the data records 21 and data tools 17 can be stored. In addition, the tool processor 27 may also optionally include a tool parsing engine 19 that is used to parse and execute instructions that form the code or script of the data tools 17. When desirable, a query along with the source database engine may be capable of functioning as the tool parsing engine without the need to store the data records in a data store.

The tool processor 27 further comprises a local communication system 25 used to establish communication between an electronic interface application 15 and the application processor 59 through the communication channel 29. The communication system 25 determines how to interface with any remote server 12*b* based on the format and type of information stored as source information 10*b* on that server 12*b*. The communication channel 29 and any other links established between the various components of the system 1 may be a dedicated facility, a Wide Area Network (WAN), a Virtual Private Network (VPN), a local area network, the internet, or any other number of other land-based, terrestrial-based or wireless communication facilities, networks, or resources.

The tool processor 27 is utilized by an electronic interface application 15, such as D3™ Remote, to access to the source information 10(*a-b*). The tool processor 27 may be selected as one from the group of a workstation, laptop computer, desktop computer, server, and any other platform that contains processing units capable of executing the data tool 55 to create data records 21.

Figure 2:
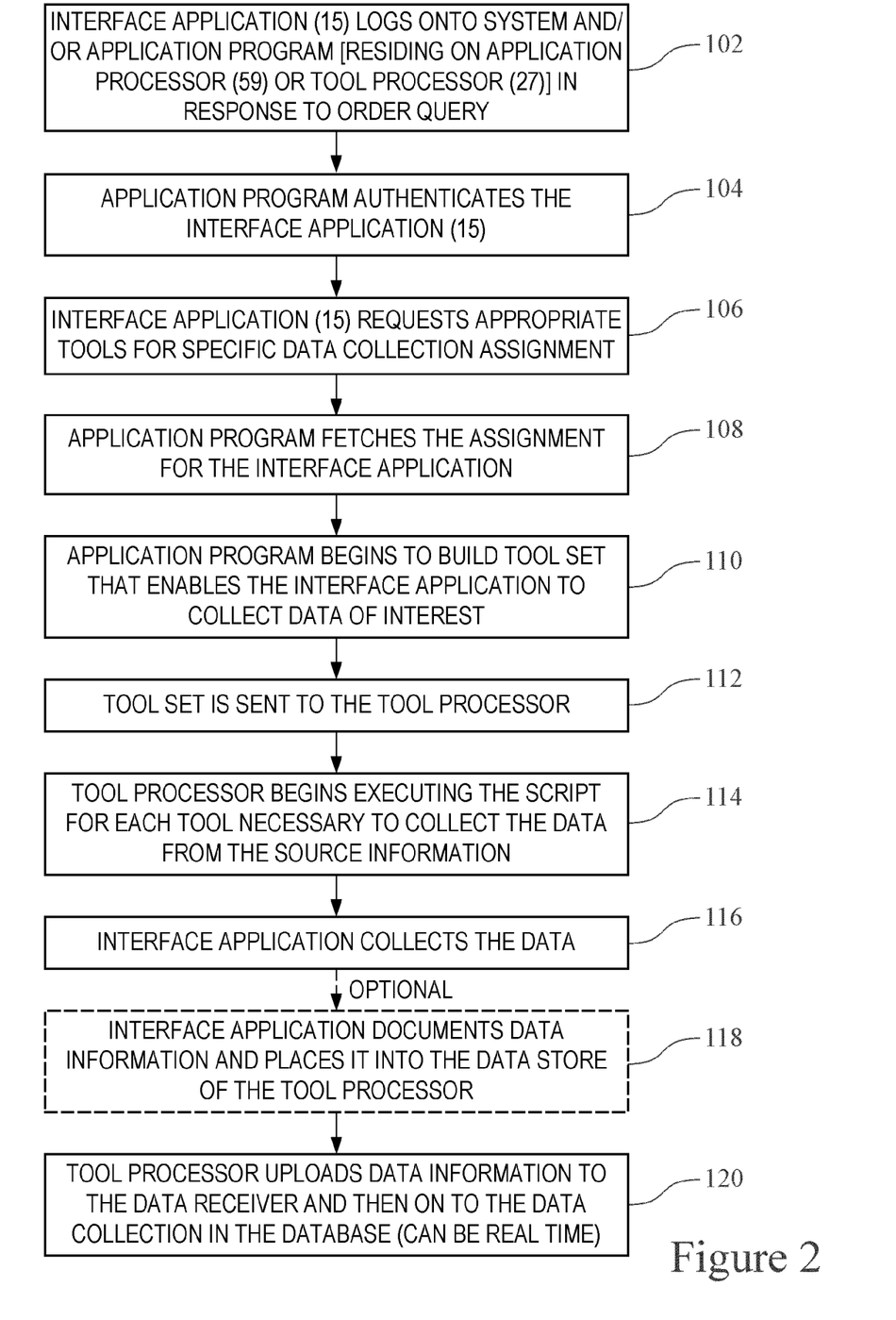
FIG. 2 is a flow chart of a method for collecting data from source information according to one aspect of the present disclosure.

Referring now to FIG. 2, a method according to the teachings of the present disclosure for collecting data from the source information 10(*a-b*) begins with a step 102 where the interface application 61 logs onto an application program or software located on the application processor 59 or tool processor 27 in response to an order 5 query. The application program includes the appropriate functionality to authenticate the identity of the interface application 61. The application program may also reside on the tool processor 27 or as part of the application processor 59 on a remote server 45. The application program may also include a combination of both of these configurations with some functions of the application program residing locally on the tool processor 27 on one server 40 and some functions of the application program residing remotely on another server 45.

The application program authenticates the interface application 15 in step 104 allowing the interface application 15 in step 106 to request the appropriate tools for a particular data collection assignment or query. In step 108 the application program retrieves the assignment for the interface application 15 and begins in step 110 to build a tool set that enables the interface application 15 to collect the information or data of interest as requested in the order 5 submitted.

The interface application 15 is a software program running on the tool processor 27 that acts as an interface between the tool processor 27 and the source information 10(*a-b*). The interface application 15 may incorporate expert systems, artificial intelligence, or other embedded intelligence programs in any software language, such as 4GL, as well as utilize interface formats or protocols, including but not limited to health level seven (HL7), open database connectivity (ODBC), and extensible markup language (XML), that are suitable for interacting with source information 10(*a-b*). The interface application 15 may reside on the same machine or server 45 as the data/tool selector function 61 and the authentication function 63 or it may reside on another machine server 40. Some functions can reside remotely or distributed across multiple servers, e.g., a distributed architecture. The interface application 15 searches through the files stored as source information 10(*a-b*) to extract data in accordance with directions from the tool set 55 and data set 57. The interface application 15 then transmits a data packet when a particular detail specified by the data set 57 and tool data 55 requests information related to a particular code. Thus the interaction application 15 supplies the search recognition and extraction skills that are necessary to generate the data records 21 during real time extraction of the data.

In step 112, the tool set is transmitted by the tool transmitter 33 within communication system 35 from the tool collection 53 within the server 45 to the tool processor 27 via the communication channel 29. The tool set is stored in the tool store 17 within the data store 23 residing on the tool processor 27. The tools are executed within the tool processor 50 in step 114. This enables the interface application 61 to create data records 21 in step 118 from the relevant data collected from the source information 10(*a-b*). The data records 21 may be stored when desirable within the data store 23 of tool processor 27. The record store 21 and the tool store 17, which reside on tool processor 27, may be contained with the same or different devices.

In step 120, the data record or records 21 can be directly transmitted from the tool processor 27 through its communication system 25 via the communication channel 29 to the data receiver 31 to a remote communication system 35 that provides a communication interface for the server 12(*a-b*). The data records 21 are stored in the data collection 51 that resides on the server 45.

In step 112, the tool set is transmitted by the tool transmitter 33 within communication system 35 from the tool collection 53 within the server 45 to the tool processor 27 via the communication channel 29. The tool set is stored in the tool store 17 within the data store 23 residing on the tool processor 27. The tools are executed within the tool processor 50 in step 114. This enables the interface application 61 to create data records 21 in step 118 from the relevant data collected from the source information 10. The data records 21 may be stored when desirable within the data store 23 of tool processor 27. The record store 21 and the tool store 17, which reside on tool processor 27, may be contained with the same or different devices.

In step 120, the data record or records 21 can be directly transmitted from the tool processor 27 through its communication system 25 via the communication channel 29 to the data receiver 31 to a remote communication system 35 that provides a communication interface for the server 12. The data records 21 are stored in the data collection 51 that resides on the server 45.

The process of building the tool set for executing the data collection assignment as described in step 110 begins with the application program identifying a tool 55 that is needed to proceed in finding the answer to the request 5. The identity of the requestor 3 may be used to determine the data collection assignment and thus serve as the basis for selecting the component tools that will comprise a tool set, although other criteria such as date, time, location and/or other relevant factors may also be used by the application program 59 in determining the tools that will comprise the tool set to compete any particular request 5. The application program 59 through the tool selector function 61 fetches the tool 55 script and the data set 57 that is linked or associated with the identified tool 55 script. The application program 59 determines when all of the tools 55 and linked or associated data sets 57 required to compete the assignment have been selected. Once all of the tools 55 and data sets 57 have been accumulated the tool set is transmitted via the communication channel 29 to the communication system 25 in the tool processor 27 as described above.

The interface application program 15 running on the tool processor 27 links the tool processor 27 to a generic interface 14 that is in communication with the sources information 10(*a-b*). This interface application 15 through the generic interface 14 searches through the source information 10(*a-b*) stored on a server 12(*a-b*) to extract data in accordance with directions in the tool set and data set. For example, the tools set may contain instructions to collect a patient's birth date, the date of an office visit, or particular codes that indicate diagnoses or events such as doctor office or hospital visits. The interface application 15 may reside on the same machine or server as the tool selector function 61, the authentication function 63 and/or the information 10(*a-b*), or on a separate machine that is interconnected with the system 1.

The generic interface 14 is a platform, such as Microsoft Dynamics® CRM, which may be used as a means for the requestor 3 to view and interact with the system 1. It may include any number of interface types, such as a web interface communicating through an application programming interface (API) to enable the platform.

The interface application 15 may logon to the application program in response to polling that occurs at predetermined intervals established during initialization of the interface application 15. The interface application 15 can be configured such that some functions reside locally on the tool processor 27 and some functions reside remotely on a server 12(*a-b*). According to another aspect of the present disclosure, the server 12(*a-b*) could also poll to see if any DCCS 13*b* are active and available to respond.

The interface application program 15 may also be part of the larger data collection and conversion system (DCCS) 13*b*. The DCCS 13*b* can be configured to reside centrally with the tool processor 27. The DCCS 13*b* can also be a distributed architecture system with some functions residing with the tool processor 27 and some functions residing remotely on another server 45. Alternatively, the interface application 15 can be configured to monitor requests 5 through the one or more data input channels that exist between the requester 3 and the server 12(*a-b*) in order to extract data in real time and deliver information in smaller data packets. The interface application 5 transmits a data packet when a particular detail specified by the data set and data tools is recognized on the data input channel. The data tool and data set may request information related to a particular code, e.g., a certain lab test has been ordered by a doctor. The interface application 15 can be configured to continuously monitor for this code and extract in real-time the fact that this test has been ordered at the same time that a doctor's assistant inputs this data into the computer resident at the doctor's office.

Figure 3:
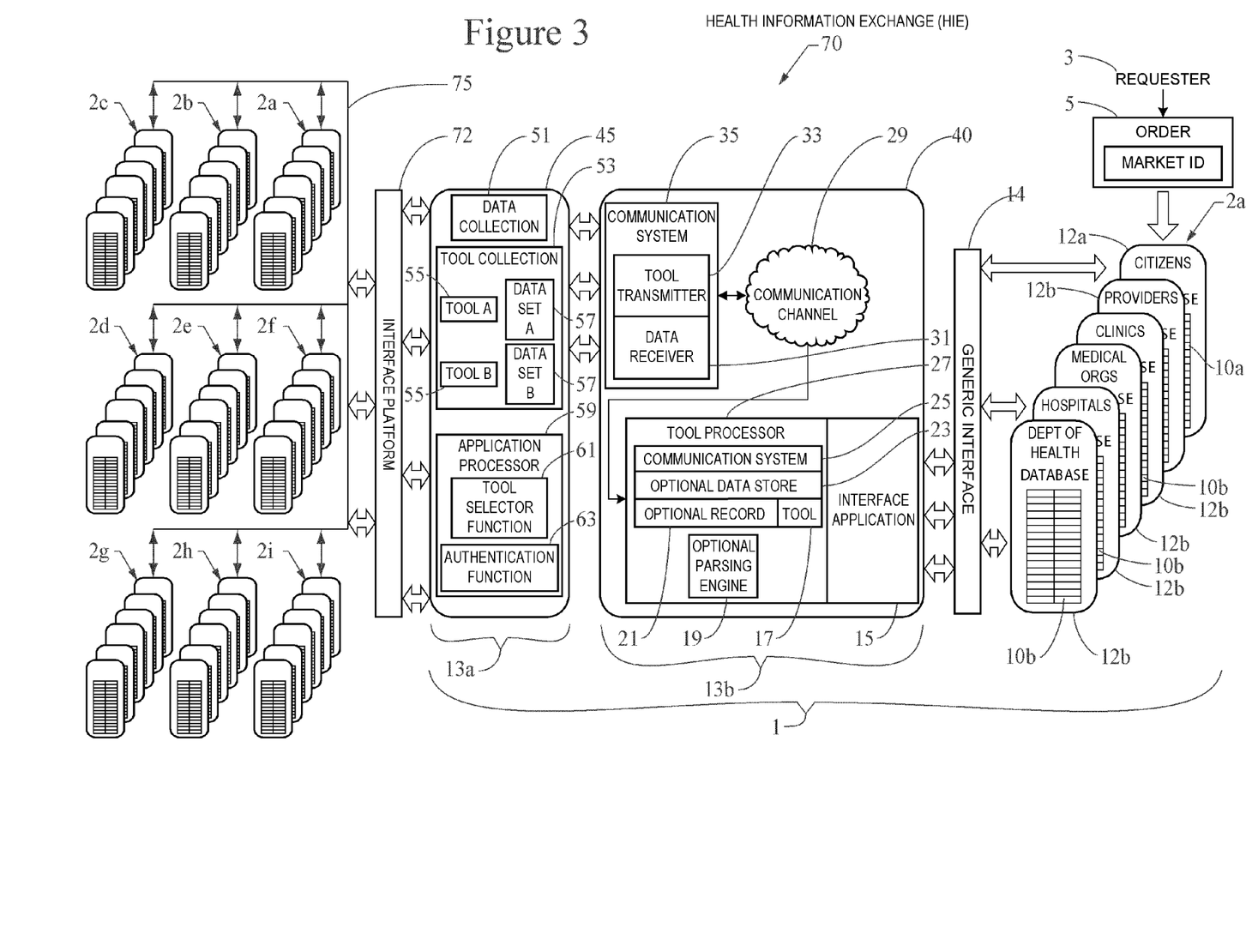
FIG. 3 is a schematic representation of a health information exchange incorporating the dynamic system according to another aspect of the present disclosure.

Referring now to FIG. 3, system 1 may be further extended to form a health information exchange (HIE) 70 by incorporating the ability to interact with source information 10*c* that reside on remote servers 12*c*. Although this information 10*c* and servers 12*c* may be part of another HIE, or a health care directive registry, i.e., 2*b*-2*i*, that is external to the health care directive registry 2*a* to which the requestor 3 belongs. Examples of registries that could be interconnected by the HIE 70 include AHCD registry, organ donor registry, disease registry, immunization registry, e-prescribing, and another regional or state HIE, among others.

One skilled-in-the-art will understand that an HIE may also include participants that may not be part of a health care directive registry, such as healthcare payers, various laboratories, hospitals, designated web portals, diagnostic imaging facilities, medication intermediaries, public health agencies, ambulatory EHRs, and other PHRs/health record banks, among others. The HIE may have any known technical architecture used to facilitate the sharing of documents within the HIE, including but not limited to a centralized architecture having a central repository, data warehouse or other database; a federated architecture having interconnected, independent databases; a health record bank, which allows patients to be more actively involved in the collection, storage, and distribution of their medical records; and a hybrid architecture being a combination of other architecture types. A more complete description of an HIE is provided in a report prepared by the University of Massachusetts Medical School Center for Health Policy and Research (CHPR) in collaboration with the National Opinion Research Center (NORC) and the National Governors Association Center for Best Practices that was presented to the State Alliance for e-Health entitled "Public Governance Models for a Sustainable Health Information Exchange Industry"; such report being made publicly available in February 2009, which is hereby incorporated by reference in its entirety.

The HIE 70 allows for any desirable number of health care directive registries and other participants in the HIE to be in communication with one another through a distributed data network 75 linked through the DMSS 13a and DCCS 13b of system 1. Preferably, an interface program 72 would act as an interface between the DMMS 13a and the various servers 12c over the distributed data network 75. Examples of an interface program 72 include, but are not limited to ProData™ (Unival Inc.) and Biztalk® (Microsoft Corp.), among others. In this system the coded data traveling to and from remote sites would be encrypted requiring a signature key that can be authenticated by the authentication function 63 in the DMSS 13a in the HIE 70.

The foregoing description of various embodiments of the present disclosure has been presented for purposes of illustration and description. It is not intended to be exhaustive or to limit the disclosure to the precise embodiments disclosed. Numerous modifications or variations are possible in light of the above teachings. The embodiments discussed were chosen and described to provide the best illustration of the principles of the present disclosure and its practical application to thereby enable one of ordinary skill in the art to utilize the disclosure in various embodiments and with various modifications as are suited to the particular use contemplated. All such modifications and variations are within the scope of the present disclosure as determined by the appended claims when interpreted in accordance with the breadth to which they are fairly, legally, and equitably entitled.

What is claimed is:

1. A dynamic computer-based system for locating and obtaining patient information, the computer-based system comprising:
   at least one hardware processor that includes memory;
   an order in the form of a query that requests information regarding a specific patient or group of patients; the information residing as source information in at least one location within multiple distributed data sources; the location within the multiple data sources identified as being on a first server; the source information including both a data collection routine and a tool collection routine; wherein the order is submitted by a user or requester;
   a document management and storage system (DMSS) having an application processor and a tool processor designed to manage and control the storage of electronic documents through the use of an application program; the application program including functionality that can select a tool and authenticate the order;
   at least one tool to send the query to the first server and retrieving the source information; the tool utilizing appropriate code to access the source information stored in the identified data source via an interface application when an appropriate request is received; the interface application being configured to continuously monitor and extract in real-time the fact that a test has been ordered at the same time the data is entered as source information into the data source;
   a communication channel that allows communication between the application processor and the tool processor; and
   a computer-based data collection and conversion system (DCCS); the DCCS linking the tool with both the DMSS and the source information;
   wherein the DMSS can reside on the first server or at a remote site from the source information;
   wherein the dynamic system locates and obtains the patient information in real-time from the location in the multiple distributed data sources.

2. The system of claim 1, wherein the order is one selected from the group of executable code; machine readable code, script, and pseudo-code.

3. The system of claim 1, wherein the order is used to identify a list of possible locations in which the source information may reside.

4. The system of claim 1, wherein the query provides at least one selected from the group of individual questions or a group of questions to be answered, a description of the type of information being sought, and the identification of a desirable response type.

5. The system of claim 4, wherein the query provides the identification of a response type; the response type being one selected from the group of a yes/no answer, a predetermined numeric value range, or an alpha text.

6. The system of claim 1, wherein the source information is comprised of at least one table or field.

7. The system of claim 1, wherein the DMSS resides on a second server; the second server being in communication with the first server through the communication channel.

8. The system of claim 1, wherein the software run by the application processor is one selected from the group of ProData™, EHMDS, or Almaga™.

9. The system of claim 8, wherein the tool is a collection of script.

10. The system of claim 9, wherein the tool is a collection of tools representing a compilation of all the different variations in which the query may be represented.

11. The system of claim 1, wherein the authentication functionality enables predetermined data collection assignments to be correlated with the request or order.

12. The system of claim 1, wherein the DCCS resides on a third server; the third server being in communication with the first and second servers via the communication channel.

13. The system of claim 1, wherein the DCCS links the tool processor and source information through the use of a generic interface.

14. The system of claim 1, wherein the DCCS is D3™.

15. The system of claim 1, wherein the DCCS is compatible with industry standard formats.

16. The system of claim 1, wherein the tool collection routine of the source information includes at least one data tool linked to a data set containing parameters, information, or data that assists the tool collection routine in using the data tool.

17. The system of claim 1, wherein the tool processor includes a data store in which data records and data tools are stored and a tool parsing engine that is used to execute instructions that form the code or script of the data tools.

18. The system of claim 1, wherein the communication channel is one selected from the group of a dedicated facility, a wide area network (WAN), a virtual private network (VPN), a local area network, and the internet.

19. The system of claim 17, wherein the tool processor is one selected from the group of a workstation, a laptop computer, a desktop computer, a server, and any other platform that contains processing units that execute the data tool to create the data records.

20. A health care directive registry, the registry comprising:
more than one organization as a member with each member maintaining a server that includes source information; the members being in communication with one another through a distributed data network; and
a dynamic computer-based system; the system comprising:
at least one hardware processor that includes memory;
an order in the form of a query that requests information regarding a specific patient or group of patients; the information residing as source information in at least one location within multiple distributed data sources; the location within the multiple data sources identified as being on a first server; the source information including both a data collection routine and a tool collection routine; wherein the order is submitted by a user or requester;
a document management and storage system (DMSS) having an application processor and a tool processor designed to manage and control the storage of electronic documents through the use of an application program; the application program including functionality that can select a tool and authenticate the order; the DMSS residing on the first server or at a remote site from the source information;
at least one tool to send the query to the first server and retrieving the source information; the tool utilizing appropriate code to access the source information stored in the identified data source via an interface application when an appropriate request is received; the interface application being configured to continuously monitor and extract in real-time the fact that a test has been ordered at the same time the data is entered as source information into the data source;
a communication channel that allows communication between the application processor and the tool processor; and
a computer-based data collection and conversion system (DCCS);
the DCCS linking the tool with both the DMSS and the source information;
wherein the dynamic system is linked to the distributed data network and used to locate and obtain patient information in real-time from the source information maintained by the members of the registry.

21. The registry of claim 20, wherein each member of the registry is selected as one from the group of a hospital, a medical provider, an insurance agency, a medical organization, a clinic, and the Department of Health.

22. A health information exchange (HIE), the HIE comprising:
a disperse data network of more than one participant as a member with each member maintaining at least one server that includes source information; and
a dynamic computer-based system; the system comprising:
at least one hardware processor that includes memory;
an order in the form of a query that requests information regarding a specific patient or group of patients; the information residing as source information in at least one location within multiple distributed data sources; the location within the multiple data sources identified as being on a first server; the source information including both a data collection routine and a tool collection routine; wherein the order is submitted by a user or requester;
a document management and storage system (DMSS) having an application processor and a tool processor designed to manage and control the storage of electronic documents through the use of an application program; the application program including functionality that can select a tool and authenticate the order; the DMSS residing on the first server or at a remote site from the source information;
at least one tool to send the query to the first server and retrieving the source information; the tool utilizing appropriate code to access the source information stored in the identified data source via an interface application when an appropriate request is received; the interface application being configured to continuously monitor and extract in real-time the fact that a test has been ordered at the same time the data is entered as source information into the data source;
a communication channel that allows communication between the application processor and the tool processor; and
a computer-based data collection and conversion system (DCCS);
the DCCS linking the tool with both the DMSS and the source information;
wherein the dynamic system is linked to the distributed data network and used to locate and obtain patient information in real-time from the source information maintained by the members of the HIE.

23. The health information exchange of claim 22, wherein the more than one participant is at least one selected from the group of health care directive registries, healthcare payers, laboratories, hospitals, designated web portals, diagnostic imaging facilities, medication intermediaries, public health agencies, ambulatory EHRs, and PHRs/health record banks.

24. A computer-based method for collecting data from source information located within multiple distributed data sources; the method comprising the steps of:
an interface application logging onto an application program that resides on an application processor or tool processor in response to a query;
the application program authenticating the interface application;
the interface application requesting appropriate tools for a specific data collection assignment;
the application program retrieving the assignment for the interface application;
the application program building a tool set with script for each tool that will enable the interface application to collect the data from the source information;
the tool set being sent to the tool processor;

the tool processor being directly linked to the source information;

the tool processor executing the script for each tool necessary to collect the data from the source information when an appropriate request is received;

the interface application collecting the desired data; and the tool processor uploading information to a data receiver and collecting the data in a database:

wherein the data collection from the multiple distributed data sources is performed in real-time; the interface application being configured to continuously monitor and extract in real-time the fact that a test has been ordered at the same time the data is entered as source information into the data source.

25. The method of claim 24 further comprising the step of having the application program create a data record and placing the data record into a data store that is in communication with the tool processor.

* * * * *